United States Patent
Smith et al.

(10) Patent No.: US 7,132,435 B2
(45) Date of Patent: Nov. 7, 2006

(54) COMPOUNDS

(75) Inventors: Mya Coral Helen Smith, Sandwich (GB); Christine Anne Louise Watson, Sandwich (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/896,112

(22) Filed: Jul. 20, 2004

(65) Prior Publication Data

US 2005/0020639 A1    Jan. 27, 2005

Related U.S. Application Data

(60) Provisional application No. 60/497,088, filed on Aug. 22, 2003.

(30) Foreign Application Priority Data

Jul. 25, 2003    (GB) .................................. 0317471.1

(51) Int. Cl.
*A61K 31/4436* (2006.01)
*A61K 31/4439* (2006.01)
*C07D 409/14* (2006.01)
*C07D 401/14* (2006.01)

(52) U.S. Cl. ................ 514/341; 546/273.4; 546/274.7; 546/276.1

(58) Field of Classification Search ............. 546/273.4, 546/274.7, 276.1; 514/341
See application file for complete search history.

(56) References Cited

U.S. PATENT DOCUMENTS

| 6,380,218 B1 | 4/2002 | Marfat et al. ................ 514/326 |
| 6,559,168 B1 | 5/2003 | Marfat et al. ................ 514/338 |
| 6,649,633 B1 | 11/2003 | Chambers et al. ........... 514/337 |
| 6,740,655 B1 | 5/2004 | Magee et al. ........... 514/255.05 |
| 2002/0111495 A1 | 8/2002 | Magee et al. ................ 546/291 |

FOREIGN PATENT DOCUMENTS

| WO | WO9845268 | 10/1998 |
| WO | WO0157025 | 8/2001 |
| WO | WO0157036 | 8/2001 |
| WO | WO0260896 | 8/2002 |
| WO | WO0368235 | 8/2003 |

OTHER PUBLICATIONS

Torphy et al., "Phosphodieterase IV Inhibitors as Therapy for Eosinophil-induced Lung Injury in Asthma", Environmental Health Perspectives, 1994, 102 Suppl. 10, p. 79-84.

Duplantier et al., "Biarylcarboxylic Acids and -amides: Inhibition of Phospodiesterase Type IV verses [$^3$H]Rolipram Binding Activity and Their Relationship to Emetic Behavior in the Ferret", J. Med. Chem., 1996, 39, p. 120-125.

Schneider et al., "Discriminative Stimulus Properties of the Stereoisomers of the Phosphodiesterase Inhibitor Rolipram", Pharmacology Biochemistry Behavior, 1995, 50, p. 211-217.

Banner and Page, "Acute versus chronic administration of phosphodiesterase inhibitors on allergen-induced pulmonary cell influx in sensitized guinea-pigs", British Journal of Pharmacology, 1995, 114, p. 93-98.

Barnette et al., "The ability of phosphodiesterase IV inhibitors to suppress superoxide production in guinea pig eosinophils is correlated with inhibition of phosphodiesterase IV catalytic activity", J. Pharmacol. Exp. Ther., 1995, 273, p. 674-679.

Wright et al., "Differential in vivo and in vitro bronchorelaxant activities of CP-80,633, a selective phosphodiesterase 4 inhibitor", Can. J. Physiol. Pharmacol., 1997, 75, p. 1001-1008.

Manabe et al., "Anti-inflammantory and bronchodilator properties of KF19514, a phosphodiesterase 4 and 1 inhibitor", European Journal of Pharmacology, 1997, 332, p. 97-107.

Ukita et al., "Novel Potent, and Selective Phosphodiesterase-4 Inhibitors as Antiasthmatic Agents: Synthesis and Biological Activities of a Series of 1-Pyridylnaphthalene Derivatives", J. of Med. Chem., 1999, 42, p. 1088-1099.

*Primary Examiner*—Patricia L. Morris
(74) *Attorney, Agent, or Firm*—Charles W. Ashbrook; Rosanna Goodman; Philip B. Polster, II

(57) ABSTRACT

This invention relates to nicotinamide derivatives of general formula (I):

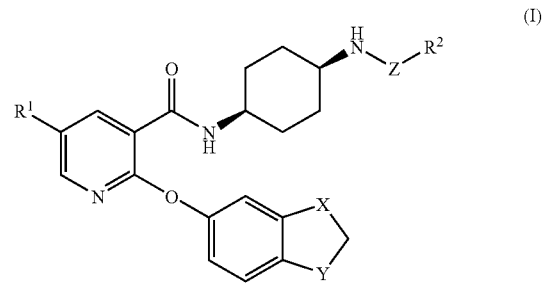

in which $R^1$, X, Y, Z and $R^2$ have the meanings defined herein, and to processes for the preparation of, intermediates used in the preparation of, compositions containing and the uses of such derivatives.

14 Claims, No Drawings

COMPOUNDS

This invention relates to nicotinamide derivatives useful as PDE4 inhibitors, and to processes for the preparations of, intermediates used in the preparation of, compositions containing and the uses of such derivatives.

The 3',5'-cyclic nucleotide phosphodiesterases (PDEs) comprise a large class of enzymes divided into at least eleven different families which are structurally, biochemically and pharmacologically distinct from one another. The enzymes within each family are commonly referred to as isoenzymes, or isozymes. A total of more than fifteen gene products is included within this class, and further diversity results from differential splicing and post-translational processing of those gene products. The present invention is primarily concerned with the four gene products of the fourth family of PDEs, i.e., PDE4A, PDE4B, PDE4C, and PDE4D. These enzymes are collectively referred to as being isoforms or subtypes of the PDE4 isozyme family.

The PDE4s are characterized by selective, high affinity hydrolytic degradation of the second messenger cyclic nucleotide, adenosine 3',5'-cyclic monophosphate (cAMP), and by sensitivity to inhibition by rolipram. A number of selective inhibitors of the PDE4s have been discovered in recent years, and beneficial pharmacological effects resulting from that inhibition have been shown in a variety of disease models (see, e.g., Torphy et al., *Environ Health Perspect.*, 1994, 102 Suppl. 10, p. 79–84 Duplantier et al., *J. Med. Chem.*, 1996, 39, p. 120–125; Schneider et al., *Pharmacol. Biochem. Behav.*, 1995, 50, p. 211–217; Banner and Page, *Br. J. Pharmacol.*, 1995, 114, p. 93–98; Barnette et al., *J. Pharmacol. Exp. Ther.*, 1995, 273, p. 674–679; Wright et al., *Can. J. Physiol. Pharmacol.*, 1997, 75, p. 1001–1008; Manabe et al., *Eur. J. Pharmacol.*, 1997, 332, p. 97–107 and Ukita et al., *J. Med. Chem.*, 1999, 42, p. 1088–1099). Accordingly, there continues to be considerable interest in the art with regard to the discovery of further selective inhibitors of PDE4s.

Successful results have already been obtained in the art with the discovery and development of selective PDE4 inhibitors. In vivo, PDE4 inhibitors reduce the influx of eosinophils to the lungs of allergen-challenged animals while also reducing the bronchoconstriction and elevated bronchial responsiveness occurring after allergen challenge. PDE4 inhibitors also suppress the activity of immune cells (including CD4+ T-lymphocytes, monocytes, mast cells, and basophils), reduce pulmonary edema, inhibit excitatory nonadrenergic noncholinergic neurotransmission (eNANC), potentiate inhibitory nonadrenergic noncholinergic neurotransmission (iNANC), reduce airway smooth muscle mitogenesis, and induce bronchodilation. PDE4 inhibitors also suppress the activity of a number of inflammatory cells associated with the pathophysiology of COPD, including monocytes/macrophages, CD4+ T-lymphocytes, eosinophils and neutrophils. PDE4 inhibitors also reduce vascular smooth muscle mitogenesis and potentially interfere with the ability of airway epithelial cells to generate pro-inflammatory mediators. Through the release of neutral proteases and acid hydrolases from their granules, and the generation of reactive oxygen species, neutrophils contribute to the tissue destruction associated with chronic inflammation, and are further implicated in the pathology of conditions such as emphysema. Therefore, PDE4 inhibitors are particularly useful for the treatment of a great number of inflammatory, respiratory and allergic diseases, disorders or conditions and for wounds and some of them are in clinical development mainly for treatment of asthma, COPD, bronchitis and emphysema.

The effects of PDE4 inhibitors on various inflammatory cell responses can be used as a basis for profiling and selecting inhibitors for further study. These effects include elevation of cAMP and inhibition of superoxide production, degranulation, chemotaxis, and tumor necrosis factor alpha (TNFa) release in eosinophils, neutrophils and monocytes.

Some nicotinamide derivatives having a PDE4 inhibitory activity have already been made. For example, the patent application WO 98/45268 discloses nicotinamide derivatives having activity as selective inhibitors of PDE4D isozyme.

The patent applications WO 01/57036 and WO 03/068235 also disclose nicotinamide derivatives which are PDE4 inhibitors useful in the treatment of various inflammatory allergic and respiratory diseases and conditions.

However, there is still a huge need for additional PDE4 inhibitors that are good drug candidates. In particular, preferred compounds should bind potently to the PDE4 enzyme whilst showing little affinity for other receptors and enzymes. They should also possess favourable pharmacokinetic and metabolic activities, be non-toxic and demonstrate few side effects. Furthermore, it is also desirable that the ideal drug candidate will exist in a physical form that is stable and easily formulated.

The present invention therefore provides new nicotinamide derivatives of formula (I):

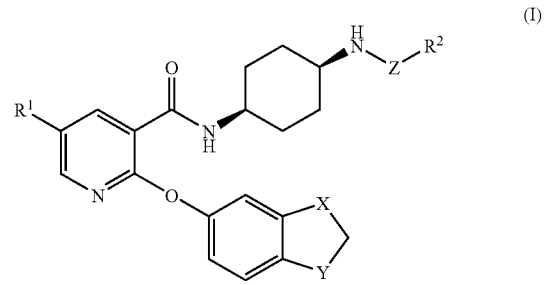

wherein
$R^1$ is selected from H, halo and $(C_1–C_4)$alkyl;
X is —$CH_2$— and Y is S or X is S and Y is —$CH_2$—;
Z is a linker group selected from CO and $SO_2$,
$R^2$ is selected from
phenyl, benzyl, naphthyl, heteroaryl and $(C_3–C_8)$cycloalkyl, each of which is optionally substituted with 1 to 3 substituents each independently selected from halo, CN, $CONR^3R^4$, $(C_1–C_6)$alkyl, $(C_1–C_6)$alkoxy, halo$(C_1–C_6)$alkyl, OH, hydroxy$(C_1–C_6)$alkyl, $(C_3–C_8)$cycloalkyl-$(C_1–C_6)$alkoxy, hydroxy$(C_2–C_6)$alkoxy, $(C_3–C_8)$cycloalkyl-$(C_1–C_6)$alkyl, $(C_3–C_8)$cycloalkyloxy, phenyl (which is optionally substituted by OH, halo and/or $(C_1–C_6)$alkoxy), $(C_3–C_8)$cycloalkyl and $NR^3R^4$; and
$R^3$ and $R^4$ are each independently selected from H, $(C_1–C_4)$ alkyl, and $SO_2(C_1–C_4$ alkyl);
a tautomer thereof or a pharmaceutically acceptable salt, solvate or polymorph of said compound or tautomer.

In the here above general formula (I), halo denotes a halogen atom selected from the group consisting of fluoro (F), chloro (Cl), bromo (Br) and iodo (I) in particular fluoro or chloro.

($C_1$–$C_4$)alkyl or ($C_1$–$C_6$)alkyl radicals denote a straight-chain or branched group containing respectively 1 to 4 or 1 to 6 carbon atoms. This also applies if they carry substituents or occur as substituents of other radicals, for example in ($C_1$–$C_6$)alkoxy, halo($C_1$–$C_6$)alkyl, hydroxy($C_1$–$C_6$)alkyl and hydroxy($C_2$–$C_6$)alkoxy radicals. Examples of suitable ($C_1$–$C_4$)alkyl and ($C_1$–$C_6$)alkyl radicals are methyl, ethyl, n-propyl, iso-propyl, n-butyl, iso-butyl, sec-butyl, tert-butyl, pentyl, hexyl etc. Examples of suitable ($C_1$–$C_6$)alkoxy and ($C_2$–$C_6$)alkoxy radicals are methoxy, ethoxy, n-propyloxy, iso-propyloxy, n-butyloxy, iso-butyloxy, sec-butyloxy and tert-butyloxy, pentoxy or hexyloxy. Hydroxy($C_1$–$C_6$)alkyl and hydroxy($C_2$–$C_6$)alkoxy radicals may contain more than one hydroxy group (—OH). According to a preferred embodiment of said invention, such radicals contain one hydroxy substituent. Examples of suitable hydroxy($C_1$–$C_6$) alkyl radicals are hydroxymethyl, 1-hydroxyethyl or 2-hydroxyethyl. Accordingly, halo($C_1$–$C_6$)alkyl radicals may contain more than one halo group.

According to the present invention, Heteroaryl means a monocyclic or polycyclic ring system comprising at least one aromatic ring, having 5 to 14 ring atoms, which ring system contains 1, 2, 3, 4 or 5 ring heteroatom(s) independently selected from N, O and S, including, where a ring nitrogen atom is present, the corresponding N-oxides and quaternary salts.

Finally, ($C_3$–$C_8$)cycloalkyl radical means a 3-membered to 8-membered saturated carbocyclic ring. Examples of suitable ($C_3$–$C_8$)cycloalkyl radicals are cyclopropyl, cyclobutyl, cyclopentyl, cyclohexyl, cycloheptyl and cyclooctyl.

It has been found that these nicotinamide derivatives are inhibitors of PDE4 isoenzymes, particularly useful for the treatment of inflammatory, respiratory and allergic diseases and conditions or for wounds.

In the general formula (I) according to the present invention, when a radical is mono- or poly-substituted, said substituent(s) can be located at any desired and chemically-feasible position(s). Also, when a radical is polysubstituted, said substituents can be identical or different, unless otherwise stated.

In one embodiment of the present invention, X is S and Y is —$CH_2$—.

In an alternative embodiment of the present invention, X is —$CH_2$— and Y is S.

Preferably, $R^1$ is H, halo, $CH_3$ or $C_2H_5$.
More preferably, $R^1$ is H, F, Cl or $CH_3$.
Most preferably, $R^1$ is F.
Preferably, $R^2$ is selected from phenyl, pyrrole, furan, furazan, thiophene, imidazole, pyrazole, oxazole, isoxazole, thiazole, isothiazole, tetrazole, triazine, pyridine, pyrazine, pyrimidine, pyridazine, indolizine, indole, isoindole, indazole, purine, naphthyridine, phthalazine, quinoline, isoquinoline, quinoxaline, quinazoline, cinnoline, benzofuran, thiadiazole, benzothiadiazole, oxadiazole, dihydrobenzofuran, benzoxadiazole, benzpyrimidine, benzothiophene, benzoxazole, benzothiazole, imidazopyridine, benzimidazole, pyrazolopyridine and pyrazolopyrimidine each of which is optionally substituted by one or more substituents selected from $CH_3$, N($CH_3$)$SO_2CH_3$, $NHSO_2CH_2CH_3$, $NHSO_2CH(CH_3)_2$, OH, $CH_2OH$, Cl, F, $C_2H_5$, $CH(CH_3)_2$, $OCH_3$, $OC_2H_4OH$, $C_2H_4OH$, $O(CH_2)_3OH$, $CF_3$, $OC_2H_5$, cyclopropylmethoxy and cyclopentyloxy.

More preferably, $R^2$ is selected from phenyl, imidazole, indazole, quinoline, quinazoline, dihydrobenzofuran, benzothiadiazole, benzoxadiazole, pyrazole, imidazopyridine, benzimidazole, pyrazolopyridine, benzyl and cyclopropyl, each of which is optionally substituted by one or more substituents selected from $CH_3$, N($CH_3$)$SO_2CH_3$, $NHSO_2CH_2CH_3$, $NHSO_2CH(CH_3)_2$, OH, $CH_2OH$, Cl, F, $C_2H_5$, $CH(CH_3)_2$, $OCH_3$, $OC_2H_4OH$, $C_2H_4OH$, $O(CH_2)_3$ OH, $CF_3$, $OC_2H_5$, cyclopropylmethoxy and cyclopentyloxy.

Yet more preferably, $R^2$ is selected from phenyl, indazole and imidazo[1,2-a]pyridine, each of which is optionally substituted by one or more substituents selected from $CH_3$, N($CH_3$)$SO_2CH_3$, $NHSO_2CH_2CH_3$, $NHSO_2CH(CH_3)_2$, OH, $CH_2OH$, Cl, F, $C_2H_5$, $CH(CH_3)_2$, $OCH_3$, $OC_2H_4OH$, $C_2H_4OH$, $O(CH_2)_3OH$, $CF_3$, $OC_2H_5$, cyclopropylmethoxy and cyclopentyloxy.

Even more preferably, $R^2$ is selected from phenyl, indazole and imidazo[1,2-a]pyridine, each of which is optionally substituted with 1 to 3 substituents each independently selected from methyl and hydroxy.

Most preferably, $R^2$ is selected from 2-hydroxy-4-methylphenyl, indazol-3-yl and imidazo[1,2-a]pyridin-8-yl.

Preferably, Z is CO.

Preferred embodiments of compounds of formula (I) are those that incorporate two or more of the foregoing preferences.

Preferably, X is S and Y is —$CH_2$—;
$R^1$ is H, halo, $CH_3$ or $C_2H_5$;
$R^2$ is selected from phenyl, imidazole, indazole, quinoline, quinazoline, dihydrobenzofuran, benzothiadiazole, benzoxadiazole, pyrazole, imidazopyridine, benzimidazole, pyrazolopyridine, benzyl and cyclopropyl, each of which is optionally substituted by one or more substituents selected from $CH_3$, N($CH_3$)$SO_2CH_3$, $NHSO_2CH_2CH_3$, $NHSO_2CH(CH_3)_2$, OH, $CH_2OH$, Cl, F, $C_2H_5$, $CH(CH_3)_2$, $OCH_3$, $OC_2H_4OH$, $C_2H_4OH$, $O(CH_2)_3OH$, $CF_3$, $OC_2H_5$, cyclopropylmethoxy and cyclopentyloxy; and
Z is CO.

More preferably, X is S and Y is —$CH_2$—;
$R^1$ is H, F, Cl or $CH_3$;
$R^2$ is selected from phenyl, indazole and imidazo[1,2-a]pyridine, each of which is optionally substituted with 1 to 3 substituents each independently selected from methyl and hydroxy; and
Z is CO.

Yet more preferably, X is S and Y is —$CH_2$—;
$R^1$ is F;
$R^2$ is selected from 2-hydroxy-4-methylphenyl, indazol-3-yl and imidazo[1,2-a]pyridin-8-yl, and
Z is CO.

Preferred compounds are:
Syn-Imidazo[1,2-a]pyridine-8-carboxylic acid (4-{[2-(2,3-dihydro-benzo[b]thiophen-6-yloxy)-5-fluoro-pyridine-3-carbonyl]-amino}-cyclohexyl)-amide,
Syn-1H-Indazole-3-carboxylic acid (4-{[2-(2,3-dihydro-benzo[b]thiophen-6-yloxy)-5-fluoro-pyridine-3-carbonyl]-amino}-cyclohexyl)-amide,
Syn-2-(2,3-Dihydro-benzo[b]thiophen-6-yloxy)-5-fluoro-N-[4-(2-hydroxy-4-methyl-benzoylamino)-cyclohexyl]-nicotinamide,
Syn-Imidazo[1,2-a]pyridine-8-carboxylic acid (4-{[2-(2,3-dihydro-benzo[b]thiophen-5-yloxy)-5-fluoro-pyridine-3-carbonyl]-amino}-cyclohexyl)-amide,
Syn-2-(2,3-Dihydro-benzo[b]thiophen-6-yloxy)-5-fluoro-N-{4-[2-(2-hydroxy-ethoxy)-benzoylamino]-cyclohexyl}-nicotinamide,
Syn-2-(2,3-Dihydro-benzo[b]thiophen-6-yloxy)-5-fluoro-N-[4-(2-hydroxy-4-hydroxymethyl-benzoylamino)-cyclohexyl]-nicotinamide, Syn-2-(2,3-Dihydro-benzo[b]thiophen-6-yloxy)-5-fluoro-N-[4-(2-hydroxy-5-hydroxymethyl-benzoylamino)-cyclohexyl]-nicotinamide,
Syn-2-(2,3-Dihydro-benzo[b]thiophen-6-yloxy)-5-fluoro-N-{4-[2-(2-hydroxy-ethoxy)-3-methyl-benzoylamino]-cyclohexyl}-nicotinamide,
Syn-2-(2,3-Dihydro-benzo[b]thiophen-6-yloxy)-5-fluoro-N-{4-[2-(2-hydroxy-ethoxy)-4-methyl-benzoylamino]-cyclohexyl}-nicotinamide,
Syn-2-(2,3-Dihydro-benzo[b]thiophen-6-yloxy)-5-fluoro-N-{4-[2-(2-hydroxy-ethoxy)-5-methyl-benzoylamino]-cyclohexyl}-nicotinamide,
Syn-N-{4-[4-Chloro-2-(2-hydroxy-ethoxy)-benzoylamino]-cyclohexyl}-2-(2,3-dihydro-benzo[b]thiophen-6-yloxy)-5-fluoro-nicotinamide,
Syn-N-{4-[5-Chloro-2-(2-hydroxy-ethoxy)-benzoylamino]-cyclohexyl}-2-(2,3-dihydro-benzo[b]thiophen-6-yloxy)-5-fluoro-nicotinamide,
Syn-2-(2,3-Dihydro-benzo[b]thiophen-6-yloxy)-N-(4-{[5-ethyl-1-(2-hydroxy-ethyl)-1H-pyrazole-3-carbonyl]-amino}-cyclohexyl)-5-fluoro-nicotinamide,
Syn-2-(2,3-Dihydro-benzo[b]thiophen-6-yloxy)-5-fluoro-N-(4-{[1-(2-hydroxy-ethyl)-5-isopropyl-1H-pyrazole-3-carbonyl]-amino}-cyclohexyl)-nicotinamide,
Syn-1-(2-Hydroxy-ethyl)-1H-indazole-3-carboxylic acid (4-{[2-(2,3-dihydro-benzo[b]thiophen-6-yloxy)-5-fluoro-pyridine-3-carbonyl]-amino}-cyclohexyl)-amide,
Syn-2-(2,3-Dihydro-benzo[b]thiophen-6-yloxy)-N-[4-(5-ethyl-2-hydroxy-benzoylamino)-cyclohexyl]-5-fluoro-nicotinamide,
Syn-N-[4-(4-Chloro-2-hydroxy-benzoylamino)-cyclohexyl]-2-(2,3-dihydro-benzo[b]thiophen-6-yloxy)-5-fluoro-nicotinamide,
Syn-2-(2,3-Dihydro-benzo[b]thiophen-6-yloxy)-5-fluoro-N-[4-(2-hydroxy-4,5-dimethyl-benzoylamino)-cyclohexyl]-nicotinamide,
Syn-2-(2,3-Dihydro-benzo[b]thiophen-6-yloxy)-N-[4-(4-ethyl-2-hydroxy-benzoylamino)-cyclohexyl]-5-fluoro-nicotinamide,
Syn-2-(2,3-Dihydro-benzo[b]thiophen-6-yloxy)-5-fluoro-N-[4-(2-hydroxy-5-methyl-benzoylamino)-cyclohexyl]-nicotinamide,
Syn-2-(2,3-Dihydro-benzo[b]thiophen-6-yloxy)-5-fluoro-N-[4-(4-fluoro-2-hydroxy-benzoylamino)-cyclohexyl]-nicotinamide,
Syn-2-(2,3-Dihydro-benzo[b]thiophen-6-yloxy)-5-fluoro-N-[4-(5-fluoro-2-hydroxy-benzoylamino)-cyclohexyl]-nicotinamide,
Syn-2-(2,3-Dihydro-benzo[b]thiophen-6-yloxy)-N-{4-[5-ethyl-2-(2-hydroxy-ethoxy)-benzoylamino]-cyclohexyl}-5-fluoro-nicotinamide,
Syn-N-[4-(5-Chloro-2-hydroxy-benzoylamino)-cyclohexyl]-2-(2,3-dihydro-benzo[b]thiophen-6-yloxy)-5-fluoro-nicotinamide,
Syn-2-(2,3-Dihydro-benzo[b]thiophen-6-yloxy)-5-fluoro-N-{4-[5-fluoro-2-(2-hydroxy-ethoxy)-benzoylamino]-cyclohexyl}-nicotinamide,
Syn-2-(2,3-Dihydro-benzo[b]thiophen-6-yloxy)-5-fluoro-N-[4-(2-hydroxy-5-trifluoromethyl-benzoylamino)-cyclohexyl]-nicotinamide, and
Syn-N-[4-(4,5-Dichloro-2-hydroxy-benzoylamino)-cyclohexyl]-2-(2,3-dihydro-benzo[b]thiophen-6-yloxy)-5-fluoro-nicotinamide,
a tautomer thereof or a pharmaceutically acceptable salt, solvate or polymorph of said compound or tautomer.
Most preferred compounds are:

Syn-Imidazo[1,2-a]pyridine-8-carboxylic acid (4-{[2-(2,3-dihydro-benzo[b]thiophen-6-yloxy)-5-fluoro-pyridine-3-carbonyl]-amino}-cyclohexyl)-amide,
Syn-1H-Indazole-3-carboxylic acid (4-{[2-(2,3-dihydro-benzo[b]thiophen-6-yloxy)-5-fluoro-pyridine-3-carbonyl]-amino}-cyclohexyl)-amide, and
Syn-2-(2,3-Dihydro-benzo[b]thiophen-6-yloxy)-5-fluoro-N-[4-(2-hydroxy-4-methyl-benzoylamino)-cyclohexyl]-nicotinamide,
a tautomer thereof or a pharmaceutically acceptable salt, solvate or polymorph of said compound or tautomer.

The nicotinamide derivatives of the formula (I) can be prepared using the Routes disclosed hereunder, and exemplified in the Examples and Preparations, in which the substituents $R^1$, $R^2$, X, Y and Z are as previously defined for the nicotinamide derivatives of the formula (I) unless otherwise stated. Other conventional methods may be used in accordance with the skilled person's knowledge.

Unless otherwise provided herein:
PyBOP® means Benzotriazol-1-yloxytris(pyrrolidino)phosphonium hexafluorophosphate;
PyBrOP® means bromo-tris-pyrrolidino-phosphonium hexafluorophosphate;
CDI means N,N'-carbonyldiimidazole;
WSCDI means 1-(3-dimethylaminopropyl)-3-ethylcarbodiimide hydrochloride;
Mukaiyama's reagent means 2-chloro-1-methylpyridinium iodide;
HATU means O-(7-Azabenzotriazol-1-yl)-N,N,N'N'-tetramethyluronium hexafluorophosphate;
HBTU means O-Benzotriazol-1-yl-N,N,N'N'-tetramethyluronium hexafluorophosphate;
DCC means N,N'-dicyclohexylcarbodiimide;
CDI means N,N'-carbonyidiimidazole;
HOAT means 1-hydroxy-7-azabenzotriazole;
HOBT means 1-hydroxybenzotriazole hydrate;
Hünig's base means N-ethyidiisopropylamine;
$Et_3N$ means triethylamine;
NMM means N-methylmorpholine;
NMP means 1-methyl-2-pyrrolidinone;
DMAP means 4-dimethylaminopyridine;
NMO means 4-methylmorpholine N-oxide;
KHMDS means potassium bis(trimethylsilyl)amide;
NaHMDS means sodium bis(trimethylsilyl)amide;
DIAD means diisopropyl azodicarboxylate;
DEAD means diethyl azodicarboxylate;
DIBAL means diisobutylammonium hydride;
Dess-Martin periodinane means 1,1,1-triacetoxy-1,1-dihydro-1,2-benziodoxol-3(1H)-one;
TBDMS-Cl means tert-butyldimethylchlorosilane;
TMS-Cl means chlorotrimethylsilane;
Boc means tert-butoxycarbonyl;
CBz means benzyloxycarbonyl;
MeOH means methanol, EtOH means ethanol, and EtOAc means ethyl acetate;
THF means tetrahydrofuran, DMSO means dimethyl sulphoxide, and DCM means dichloromethane; DMF means N,N-dimethylformamide;
ACOH means acetic acid, TFA means trifluoroacetic acid; rt means room temperature; 3° means tertiary; eq means equivalents; Me means methyl, Et means ethyl, Bn means benzyl; other abbreviations are used in accordance with standard synthetic chemistry practice.

Route A

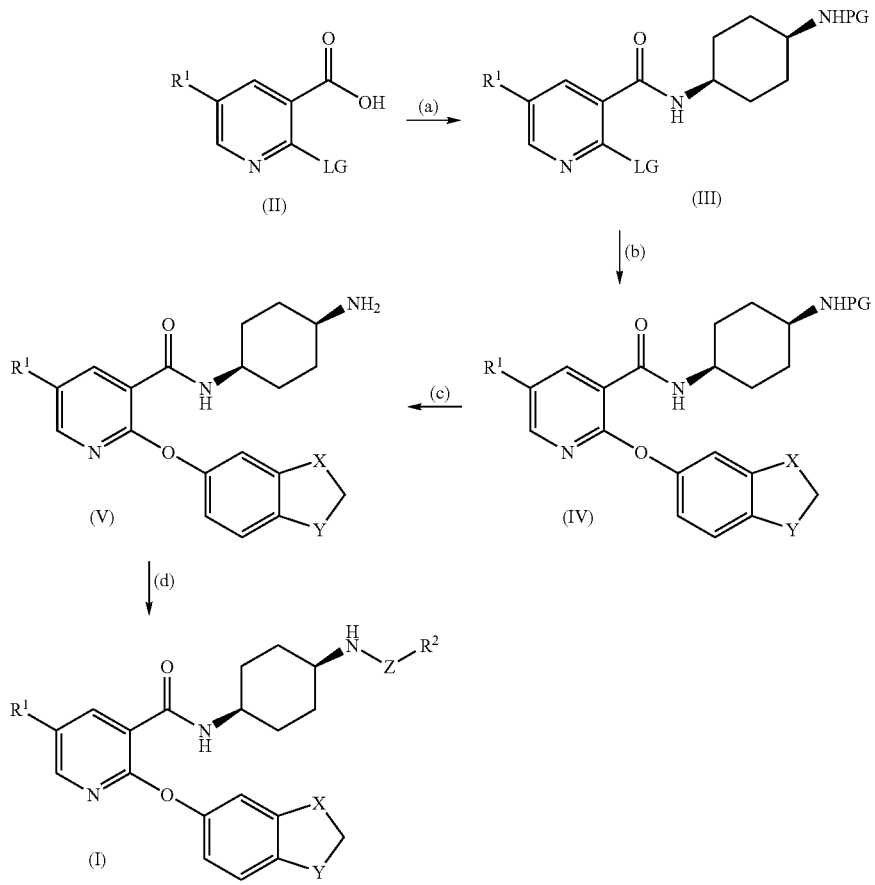

LG = Leaving Group
PG = Amine Protecting Group

Nicotinic acids of formula (II) are either available commercially or may be obtained by analogy with the methods of Haylor et. al. (EP 0634413). The protected cyclohexylamines are either available commercially or may be prepared by analogy with the method of Oku et. al. (WO 99/54284). The benzothiophenols may be prepared by analogy to the methods of Gymer et. al (WO 02/18333) and Malmström et. al. (J. Am. Chem. Soc., 2001, 123, 3434–3440).

In the scheme above, $R^1$, $R^2$, Z, X and Y are as previously defined, PG is a suitable amine protecting group, typically Boc, CBz or Bn, and preferably Boc, and LG is a suitable leaving group, typically halo, and preferably Cl.

(a)—Amide Bond Formation is conducted by reaction of nicotinic acid (II) with a cyclohexane-1,4-diamine (in which one amine function is protected by PG, a suitable amine protecting group e.g. Boc, Bn, preferably Boc) to form amide (III). This acid/amine coupling may be undertaken by using either (i) an acyl chloride derivative of acid (II)+amine, with an excess of acid acceptor in a suitable solvent, or
(ii) the acid (II) with a conventional coupling agent+amine, optionally in the presence of a catalyst, with an excess of acid acceptor in a suitable solvent.

Typically, the reaction is conducted under the following conditions:

(i) acid chloride of acid (II) (generated in-situ), an excess of amine, optionally with an excess of 3° amine such as $Et_3N$, Hünig's base or NMM, in DCM or THF, without heating for 1 to 24 hrs, or (ii) acid (II), WSCDI/DCC/CDI, optionally in the presence of HOBT/HOAT, an excess of amine, with an excess of NMM, $Et_3N$, Hünig's base in THF, DCM or EtOAc, at rt. for 4 to 48 hrs; or, acid (II), PYBOP®/PyBrOP®/Mukaiyama's reagent, an excess of amine, with an excess of NMM, $Et_3N$, Hünig's base in THF, DCM or EtOAc, at rt. for 4 to 24 hrs.

The preferred conditions comprise treatment of a solution of acid (II) in DCM and DMF with oxalyl chloride and stirring at RT for 18 hours (to give the acid chloride), followed by the addition of a solution of the amine and Hünig's base in DCM and stirring for 18 hours at RT.

(b)—Ether Formation is conducted by substitution of leaving group LG, (e.g. Hal, preferably Cl) of (III) with an excess of 2,3-dihydro-benzo[b]thiophen-6-ol or 2,3-dihydro-benzo[b]thiophen-5-ol to give compound (IV), in the presence of a base in a suitable solvent (e.g. MeCN, dioxan).

Typically, the reaction is conducted using an alkali metal salt as the base (e.g. $Cs_2CO_3$, $K_2CO_3$) in a suitable solvent (e.g. MeCN or dioxan) at elevated temperature.

(c)—Amine Deprotection comprises removal of the protecting group, PG, from (IV) to give amine (V) by a method selective to the protecting group as detailed by Greene et al in "Protective Groups in Organic Synthesis".

Typically, when PG=Boc, the reaction comprises treatment of (IV) with a strong acid (e.g. TFA, HCl), in a suitable solvent (e.g. dioxan, DCM) at room temperature.

Preferably, when PG=Boc, the reaction comprises treatment of a solution of (IV) in DCM with TFA at RT for 4 hours.

(d)—Reaction of amino group with T-Z-$R^2$

Compounds of the formula (I) may be prepared by reaction of amine (V) with a suitable reagent of formula T-Z-$R^2$, where T represents OH or Cl. When Z represents CO, and T represents OH or Cl, compounds of formula (I) may be prepared by reaction of the amine of formula (V) with $R^2CO_2H$ according to the general methods described previously for step (a).

The preferred conditions are: WSCDI, HOBT, amine (V), $R^2CO_2H$, an excess of 3° amine base (Hünig's base, $Et_3N$ or NMM) in dichloromethane, N,N-dimethylformamide, NMP or DMA, at rt. for up to 36 hrs, or amine (V), acid $R^2CO_2H$, HBTU in the presence of an excess of 3° amine base (Hünig's base, $Et_3N$ or NMM) in DMF for up to 24 hrs at rt.

When Z represents $SO_2$ and T represents Cl, compounds of formula (I) may be prepared by reaction of the amine of formula (V) with $R^2SO_2Cl$ by analogy with the general methods described in step (a).

The preferred conditions are: WSCDI, HOBT, amine (V), $R^2SO_2Cl$, an excess of 3° amine base (Hünig's base, $Et_3N$ or NMM) in N,N-dimethylformamide, at rt. for 18 hrs, or amine (V), $R^2SO_2Cl$ in the presence of excess $Et_3N$ in dichloromethane at rt.

Compounds of formula $R^2ZT$, are either commercially available, or may be obtained using standard methodology, or when $R^2$ is a heterocycle, by analogy with the methods described in Comprehensive Heterocyclic Chemistry I and II (Elsevier Science Ltd.) and references therein.

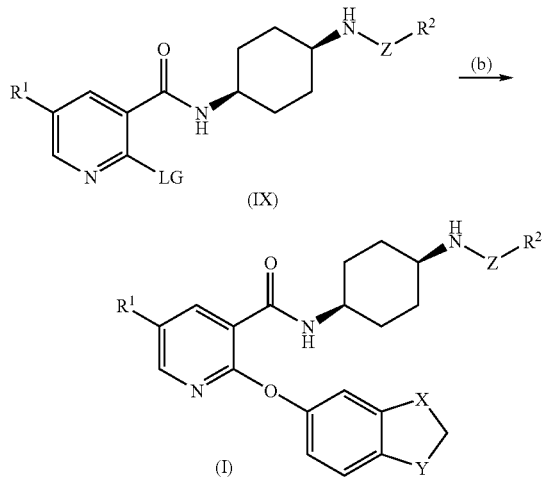

The compound of formula (VII) may be prepared from the amine (VI) by reaction with $R^2ZY$ according to the methods described previously in step (d), Route A.

The compound of formula (VIII) may be prepared from the compound of formula (VII) by analogy to the methods described previously in step (c), Route A.

Compounds of formula (IX) may be prepared by reaction of the amine of formula (VIII) with the acid (II) according to the methods described previously in step (a), Route A.

Compounds of formula (I) may be prepared by reaction of compounds of formula (IX) with 2,3-dihydro-benzo[b]thiophen-6-ol or 2,3-dihydro-benzo[b]thiophen-5-ol as described previously in step (b), Route A.

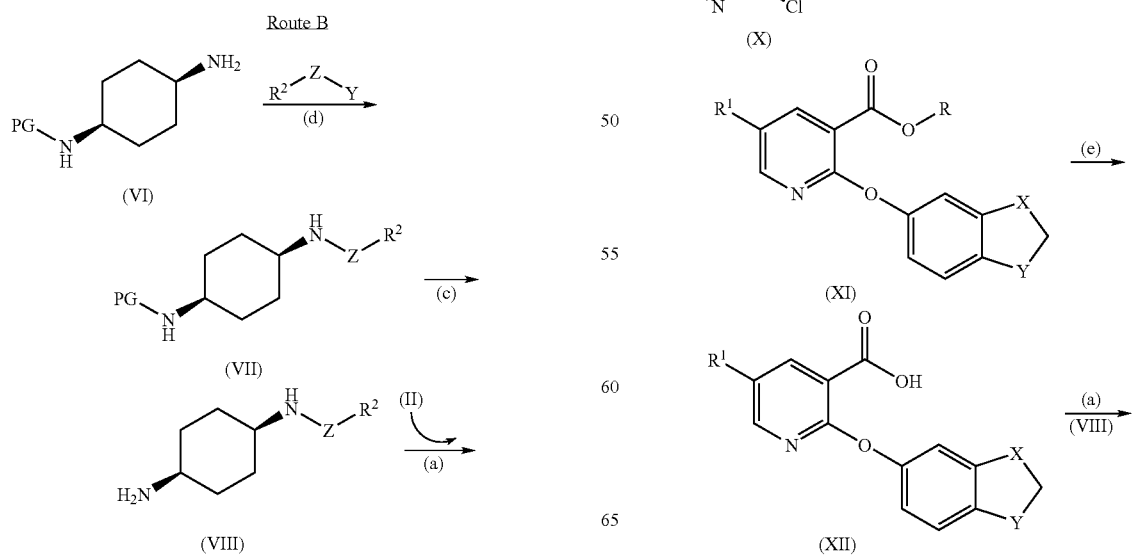

-continued

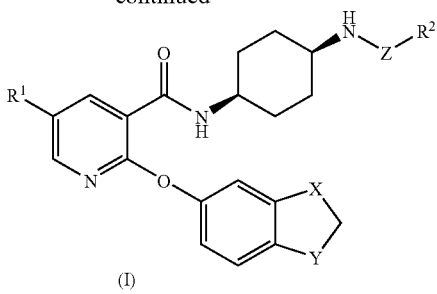

(I)

R represents a carboxylic acid protecting group (e.g. lower alkyl, Bn, typically lower alkyl, preferably ethyl).

Compounds of formula (X) are either available commercially or may be obtained from the compounds of formula (II), using standard esterification conditions.

Compounds of formula (XI) may be prepared by reaction of the ester (X) with 2,3-dihydro-benzo[b]thiophen-6-ol or 2,3-dihydro-benzo[b]thiophen-5-ol, as described previously in step (b), Route A.

Step (e)-Ester hydrolysis

Hydrolysis of the ester (XI) may be achieved in the presence of acid or base, in a suitable solvent, optionally at elevated temperature to afford the acid (XII).

Typically, the ester (XI) is treated with an alkali metal hydroxide (eg Li, Na, Cs) in aqueous solvent (MeOH, EtOH, dioxan, THF) at between rt and the reflux temperature of the reaction, to give the acid of formula (XII)

Reaction of the acid (XII) with the amine (VIII) as described previously in step (a) provides the compounds of formula (I).

Alternatively compounds of formula (XII) may be prepared by reaction of the nicotinic acids of formula (II) with 2,3-dihydro-benzo[b]thiophen-6-ol or 2,3-dihydro-benzo[b]thiophen-5-ol, as described previously in step (b), Route A.

Further Routes

Certain $R^2$ groups may undergo further functional group interconversions (FGIs) and transformations, such as alkylation of a phenol hydroxy group, using a suitable alkylbromide, in the presence of a suitable alkali metal base (such as $K_2CO_3$), optionally in the presence of a catalyst (eg KI) in a suitable solvent such as acetonitrile and/or N,N-dimethylformamide at elevated temperature, or demethylation of a methoxy group by treatment with lithium iodide in pyridine or collidine, or by treatment with $BBr_3$ in dichloromethane.

For certain compounds of the description, a suitable protecting group strategy may be employed. For example, a hydroxyl group may be protected using a tetrahydropyran group, and deprotection may be achieved by treatment with a solution of acetic acid:water:tetrahydrofuran (4:1:2 by volume) at rt. for upto 18 hrs. Further, a benzyloxy group may be used and deprotected to give the corresponding hydroxyl compound, for example by using a reduction (e.g. with palladium black in acid).

All of the above reactions and the preparations of novel starting materials used in the preceding methods are conventional and appropriate reagents and reaction conditions for their performance or preparation as well as procedures for isolating the desired products will be well-known to those skilled in the art with reference to literature precedents and the examples and preparations hereto.

As mentioned above, use of protection/deprotection strategies are needed in some instances. Methods such as those described by T. W. GREENE (*Protective Groups in Organic Synthesis*, A. Wiley-Interscience Publication, 1981) or by McOMIE (*Protective Groups in Organic Chemistry*, Plenum Press, 1973), can be used.

Compounds of formula (I), as well as intermediate for the preparation thereof can be purified according to various well-known methods, such as for example crystallization or chromatography.

The nicotinamide derivatives of formula (I) may also be optionally transformed in pharmaceutically acceptable salts. In particular, these pharmaceutically acceptable salts of the nicotinamide derivatives of the formula (I) include the acid addition and the base salts (including disalts) thereof.

Suitable acid addition salts are formed from acids which form non-toxic salts. Examples include the acetate, aspartate, benzoate, besylate, bicarbonate/carbonate, bisulphate, camsylate, citrate, edisylate, esylate, fumarate, gluceptate, gluconate, glucuronate, hibenzate, hydrochloride/chloride, hydrobromide/bromide, hydroiodide/iodide, hydrogen phosphate, isothionate, D- and L-lactate, malate, maleate, malonate, mesylate, methylsulphate, 2-napsylate, nicotinate, nitrate, orotate, palmoate, phosphate, saccharate, stearate, succinate, sulphate, D- and L-tartrate, 1-hydroxy-2-naphtoate, 3-hydroxy-2-naphthoate and tosylate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

For a review on suitable salts, see Stahl and Wermuth, Handbook of Pharmaceutical Salts: Properties, Selection and Use, Wiley-VCH, Weinheim, Germany (2002).

A pharmaceutically acceptable salt of a nicotinamide derivative of the formula (I) may be readily prepared by mixing together solutions of the nicotinamide derivative of formula (I) and the desired acid or base, as appropriate. The salt may precipitate from solution and be collected by filtration or may be recovered by evaporation of the solvent.

Pharmaceutically acceptable solvates in accordance with the invention include hydrates and solvates wherein the solvent of crystallization may be isotopically substituted, e.g. $D_2O$, $d_6$-acetone, $d_6$-DMSO.

Also within the scope of the invention are clathrates, drug-host inclusion complexes wherein, in contrast to the aforementioned solvates, the drug and host are are present in non-stoichiometric amounts. For a review of such complexes, see J Pharm Sci, 64 (8), 1269–1288 by Haleblian (August 1975).

Hereinafter all references to nicotinamide derivatives of formula (I) include references to salts thereof and to solvates and clathrates of compounds of formula (I) and salts thereof.

The invention includes all polymorphs of the nicotinamide derivatives of formula (I).

Also within the scope of the invention are so-called dimethylformamide, "prodrugs" of the nicotinamide derivatives of formula (I). Thus certain derivatives of nicotinamide derivatives of formula (I) which have little or no pharmacological activity themselves can, when metabolised upon administration into or onto the body, give rise to nicotinamide derivatives of formula (I) having the desired activity. Such derivatives are referred to as "prodrugs".

Prodrugs in accordance with the invention can, for example, be produced by replacing appropriate functionalities present in the nicotinamide derivatives of formula (I) with certain moieties known to those skilled in the art as "pro-moieties" as described, for example, in "Design of Prodrugs" by H Bundgaard (Elsevier, 1985).

Finally, certain nicotinamide derivatives of formula (I) may themselves act as prodrugs of other nicotinamide derivatives of formula (I).

Nicotinamide derivatives of formula (I) containing one or more asymmetric carbon atoms can exist as two or more optical isomers. Where a nicotinamide derivative of formula (I) contains an alkenyl or alkenylene group, geometric cis/trans (or Z/E) isomers are possible, and where the nicotinamide derivative contains, for example, a keto or oxime group, tautomeric isomerism ('tautomerism') may occur. It follows that, unless otherwise defined, a single nicotinamide derivative may exhibit more than one type of isomerism.

Included within the scope of the present invention are all optical isomers, geometric isomers and tautomeric forms of the nicotinamide derivatives of formula (I), including compounds exhibiting more than one type of isomerism, and mixtures of one or more thereof.

Cis/trans isomers may be separated by conventional techniques well known to those skilled in the art, for example, fractional crystallisation and chromatography.

Conventional techniques for the preparation/isolation of individual stereoisomers include the conversion of a suitable optically pure precursor, resolution of the racemate (or the racemate of a salt or derivative) using, for example, chiral HPLC, or fractional crystallisation of diastereoisomeric salts formed by reaction of the racemate with a suitable optically active acid or base, for example, tartaric acid.

The present invention also includes all pharmaceutically acceptable isotopic variations of a nicotinamide derivative of formula (I). An isotopic variation is defined as one in which at least one atom is replaced by an atom having the same atomic number, but an atomic mass different from the atomic mass usually found in nature.

Examples of isotopes suitable for inclusion in the nicotinamide derivatives of the invention include isotopes of hydrogen, such as $^2$H and $^3$H, carbon, such as $^{13}$C and $^{14}$C, nitrogen, such as $^{15}$N, oxygen, such as $^{17}$O and $^{18}$O, phosphorus, such as $^{32}$P, sulphur, such as $^{35}$S, fluorine, such as $^{18}$F, and chlorine, such as $^{36}$Cl.

Substitution of the nicotinamide derivative of formula (I) isotopes such as deuterium, i.e. $^2$H, may afford certain therapeutic advantages resulting from greater metabolic stability, for example, increased in vivo half-life or reduced dosage requirements, and hence may be preferred in some circumstances.

Certain isotopic variations of the nicotinamide derivatives of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Isotopic variations of the nicotinamide derivatives of formula (I) can generally be prepared by conventional techniques known to those skilled in the art or by processes analogous to those described in the accompanying Examples and Preparations using appropriate isotopic variations of suitable reagents.

According to a further aspect, the present invention concerns mixtures of nicotinamide derivatives of the formula (I), as well as mixtures with or of their pharmaceutically acceptable salts, solvates, polymorphs, isomeric forms and/or isotope forms.

According to the present invention, all the here above mentioned forms of the nicotinamide derivatives of formula (I) except the pharmaceutically acceptable salts (i.e. said solvates, polymorphs, isomeric forms and isotope forms), are defined as "derived forms" of the nicotinamide derivatives of formula (I) in what follows.

The nicotinamide derivatives of formula (I), their pharmaceutically acceptable salts and/or derived forms, are valuable pharmaceutical active compounds, which are suitable for the therapy and prophylaxis of numerous disorders in which the PDE4 enzymes are involved, in particular the inflammatory disorders, allergic disorders, respiratory diseases and wounds.

The nicotinamide derivatives of formula (I) and their pharmaceutically acceptable salts and derived forms as mentioned above can be administered according to the invention to animals, preferably to mammals, and in particular to humans, as pharmaceuticals for therapy or prophylaxis. They can be administered per se, in mixtures with one another or in combination with other drugs, or in the form of pharmaceutical preparations which permit enteral (gastric) or parenteral (non-gastric) administration and which as active constituent contain an efficacious dose of at least one nicotinamide derivative of the formula (I), its pharmaceutically acceptable salts and/or derived forms, in addition to customary pharmaceutically innocuous excipients and/or additives. The term "excipient" is used herein to describe any ingredient other than the compound of the invention. The choice of excipient will to a large extent depend on the particular mode of administration.

The nicotinamide derivatives of formula (I), their pharmaceutically acceptable salts and/or derived forms may be freeze-dried, spray-dried, or evaporatively dried to provide a solid plug, powder, or film of crystalline or amorphous material. Microwave or radio frequency drying may be used for this purpose.

Oral Administration

The nicotinamide derivatives of formula (I) their pharmaceutically acceptable salts and/or derived forms of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, films (including muco-adhesive), ovules, sprays and liquid formulations.

Liquid formulations include suspensions, solutions, syrups and elixirs. Such formulations may be employed as fillers in soft or hard capsules and typically comprise a carrier, for example, water, ethanol, propylene glycol, methylcellulose, or a suitable oil, and one or more emulsifying agents and/or suspending agents. Liquid formulations may also be prepared by the reconstitution of a solid, for example, from a sachet.

The nicotinamide derivatives of formula (I), their pharmaceutically acceptable salts and/or derived forms of the invention may also be used in fast-dissolving, fast-disintegrating dosage forms such as those described in Expert Opinion in Therapeutic Patents, 11 (6), 981–986 by Liang and Chen (2001).

The composition of a typical tablet in accordance with the invention may comprise:

| Ingredient | % w/w |
|---|---|
| Nicotinamide derivative of formula (I) | 10.00* |
| Microcrystalline cellulose | 64.12 |
| Lactose | 21.38 |
| Croscarmellose sodium | 3.00 |
| Magnesium stearate | 1.50 |

*Quantity adjusted in accordance with drug activity.

A typical tablet may be prepared using standard processes known to a formulation chemist, for example, by direct compression, granulation (dry, wet, or melt), melt congealing, or extrusion. The tablet formulation may comprise one or more layers and may be coated or uncoated.

Examples of excipients suitable for oral administration include carriers, for example, cellulose, calcium carbonate, dibasic calcium phosphate, mannitol and sodium citrate, granulation binders, for example, polyvinylpyrrolidine, hydroxypropylcellulose, hydroxypropylmethylcellulose and gelatin, disintegrants, for example, sodium starch glycolate and silicates, lubricating agents, for example, magnesium stearate and stearic acid, wetting agents, for example, sodium lauryl sulphate, preservatives, anti-oxidants, flavours and colourants.

Solid formulations for oral administration may be formulated to be immediate and/or modified release. Modified release formulations include delayed-, sustained-, pulsed-, controlled dual-, targeted and programmed release. Details of suitable modified release technologies such as high energy dispersions, osmotic and coated particles are to be found in Verma et al, Pharmaceutical Technology On-line, 25(2), 1–14 (2001). Other modified release formulations are described in U.S. Pat. No. 6,106,864.

Parenteral Administration

The nicotinamide derivatives of formula (I), their pharmaceutically acceptable salts and/or derived forms of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of nicotinamide derivatives of formula (I) used in the preparation of parenteral solutions may be increased by suitable processing, for example, the use of high energy spray-dried dispersions (see WO 01/47495) and/or by the use of appropriate formulation techniques, such as the use of solubility-enhancing agents.

Formulations for parenteral administration may be formulated to be immediate and/or modified release. Modified release formulations include delayed-, sustained-, pulsed-, controlled dual-, targeted and programmed release.

Topical Administration

The nicotinamide derivatives of the invention may also be administered topically to the skin or mucosa, either dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin and propylene glycol. Penetration enhancers may be incorporated—see, for example, J Pharm Sci, 88 (10), 955–958 by Finnin and Morgan (October 1999).

Other means of topical administration include delivery by iontophoresis, electroporation, phonophoresis, sonophoresis and needle-free or microneedle injection.

Formulations for topical administration may be formulated to be immediate and/or modified release. Modified release formulations include delayed-, sustained-, pulsed-, controlled dual-, targeted and programmed release. Thus nicotinamide derivatives of formula (I) may be formulated in a more solid form for administration as an implanted depot providing long-term release of the active compound.

Inhaled/Intranasal Administration

The nicotinamide derivatives of formula (I) can also be administered intranasally or by inhalation, typically in the form of a dry powder (either alone, as a mixture, for example, in a dry blend with lactose in anhydrous or monohydrate form, preferably monohydrate, mannitol, dextran, glucose, maltose, sorbitol, xylitol, fructose, sucrose or trehalose, or as a mixed component particle, for example, mixed with phospholipids) from a dry powder inhaler or as an aerosol spray from a pressurised container, pump, spray, atomiser (preferably an atomiser using electrohydrodynamics to produce a fine mist), or nebuliser, with or without the use of a suitable propellant, such as dichlorofluoromethane.

The pressurised container, pump, spray, atomizer, or nebuliser contains a solution or suspension of the active compound comprising, for example, ethanol (optionally, aqueous ethanol) or a suitable alternative agent for dispersing, solubilising, or extending release of the active, the propellant(s) as solvent and an optional surfactant, such as sorbitan trioleate or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

A suitable solution formulation for use in an atomiser using electrohydrodynamics to produce a fine mist may contain from 1 µg to 20 mg of the nicotinamide derivative of formula (I) per actuation and the actuation volume may vary from 1 µl to 100 µl. A typical formulation may comprise a nicotinamide derivative of formula (I), propylene glycol, sterile water, ethanol and sodium chloride. Alternative solvents which may be used instead of propylene glycol include glycerol and polyethylene glycol.

Capsules, blisters and cartridges (made, for example, from gelatin or HPMC) for use in an inhaler or insufflator may be formulated to contain a powder mix of the nicotinamide derivative of formula (I), a suitable powder base such as lactose or starch and a performance modifier such as I-leucine, mannitol, or magnesium stearate.

In the case of dry powder inhalers and aerosols, the dosage unit is determined by means of a valve which delivers a metered amount. Units in accordance with the invention are typically arranged to administer a metered dose or "puff" containing from 1 µg to 4000 µg of the nicotinamide derivative of formula (I). The overall daily dose will typically be in the range 1 µg to 20 mg which may be administered in a single dose or, more usually, as divided doses throughout the day.

Formulations for inhaled/intranasal administration may be formulated to be immediate and/or modified release. Modified release formulations include delayed-, sustained-, pulsed-, controlled dual-, targeted and programmed release. Sustained or controlled release can be obtained by using for example poly(D,L-lactic-co-glycolic acid).

Flavouring agents, such as methol and levomethol and/or sweeteners such as saccharing or saccharin sodium can be added to the formulation.

Rectal/Intravaginal Administration

The nicotinamide derivatives of formula (I) may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled dual-, targeted and programmed release.

Ocular/Andial Administration

The nicotinamide derivatives of formula (I) may also be administered directly to the eye or ear, typically in the form of drops of a micronised suspension or solution in isotonic, pH-adjusted, sterile saline. Other formulations suitable for ocular and andial administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/andial administration may be formulated to be immediate and/or modified release. Modified release formulations include delayed-, sustained-, pulsed-, controlled dual-, targeted, or programmed release.

Enabling Technologies

The nicotinamide derivatives of formula (I) may be combined with soluble macromolecular entities such as cyclodextrin or polyethylene glycol-containing polymers to improve their solubility, dissolution rate, taste-masking, bioavailability and/or stability.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Dosage

For administration to human patients, the total daily dose of the nicotinamide derivatives of formula (I) is typically in the range 0.001 mg/kg to 100 mg/kg depending, of course, on the mode of administration. The total daily dose may be administered in single or divided doses. The physician will readily be able to determine doses for subjects depending on age, weight, health state and sex or the patient as well as the severity of the disease.

According to another embodiment of the present invention, the nicotinamide derivatives of the formula (I), their pharmaceutically acceptable salts and/or their derived forms, can also be used as a combination with one or more additional therapeutic agents to be co-administered to a patient to obtain some particularly desired therapeutic end result. The second and more additional therapeutic agents may also be a nicotinamide derivatives of the formula (I), their pharmaceutically acceptable salts and/or their derived forms, or one or more PDE4 inhibitors known in the art. More typically, the second and more therapeutic agents will be selected from a different class of therapeutic agents.

As used herein, the terms "co-administration", "co-administered" and "in combination with", referring to the nicotinamide derivatives of formula (I) and one or more other therapeutic agents, is intended to mean, and does refer to and include the following:

simultaneous administration of such combination of nicotinamide derivative(s) and therapeutic agent(s) to a patient in need of treatment, when such components are formulated together into a single dosage form which releases said components at substantially the same time to said patient, substantially simultaneous administration of such combination of nicotinamide derivative(s) and therapeutic agent(s) to a patient in need of treatment, when such components are formulated apart from each other into separate dosage forms which are taken at substantially the same time by said patient, whereupon said components are released at substantially the same time to said patient, sequential administration of such combination of nicotinamide derivative(s) and therapeutic agent(s) to a patient in need of treatment, when such components are formulated apart from each other into separate dosage forms which are taken at consecutive times by said patient with a significant time interval between each administration, whereupon said components are released at substantially different times to said patient; and sequential administration of such combination of nicotinamide derivative(s) and therapeutic agent(s) to a patient in need of treatment, when such components are formulated together into a single dosage form which releases said components in a controlled manner whereupon they are concurrently, consecutively, and/or overlappingly administered at the same and/or different times by said patient.

Suitable examples of other therapeutic agents which may be used in combination with the nicotinamide derivatives of the formula (I), their pharmaceutically acceptable salts and/ or their derived forms include, but are by no mean limited to:

(a) 5-Lipoxygenase (5-LO) inhibitors or 5-lipoxygenase activating protein (FLAP) antagonists,
(b) Leukotriene antagonists (LTRAs) including antagonists of LTB4, LTC4, LTD4, and LTE4, (c) Histaminic receptor antagonists including H1, H3 and H4 antagonists,
(d) α1- and α2-adrenoceptor agonist vasoconstrictor sympathomimetic agents for decongestant use,
(e) Muscarinic M3 receptor antagonists or anticholinergic agents,
(f) β2-adrenoceptor agonists,
(g) Theophylline,
(h) Sodium cromoglycate,
(i) COX-1 inhibitors (NSAIDs) and COX-2 selective inhibitors,
(j) Oral or inhaled Glucocorticosteroids,
(k) Monoclonal antibodies active against endogenous inflammatory entities,
(l) Anti-tumor necrosis factor (anti-TNF-a) agents,
(m) Adhesion molecule inhibitors including VLA-4 antagonists,
(n) Kinin-B1—and B2-receptor antagonists,
(o) Immunosuppressive agents,
(p) Inhibitors of matrix metalloproteases (MMPs),
(q) Tachykinin NK1, NK2 and NK3 receptor antagonists,
(r) Elastase inhibitors,
(s) Adenosine A2a receptor agonists,
(t) Inhibitors of urokinase,
(u) Compounds that act on dopamine receptors, e.g. D2 agonists,
(v) Modulators of the NFkb pathway, e.g. IKK inhibitors,
(w) Agents that can be classed as mucolytics or anti-tussive,
(x) antibiotics, and
(y) p38 MAP kinase inhibitors According to the present invention, combination of the nicotinamide derivatives of formula (I) with:
muscarinic M3 receptor agonists or anticholinergic agents including in particular ipratropium salts, namely bromide, tiotropium salts, namely bromide, oxitropium salts, namely bromide, perenzepine, and telenzepine,
p38 MAP kinase inhibitors,
H3 antagonists,
β2-adrenoceptor agonists including albutarol, salbutamol, formoterol and salmeterol,
glucocorticosteroids, in particular inhaled glucocorticosteroids with reduced systemic side effects, including prednisone, prednisolone, flunisolide, triamcinolone acetonide, beclomethasone dipropionate, budesonide, fluticasone propionate, and mometasone furoate,
or adenosine A2a receptor agonists, are preferred.

It is to be appreciated that all references herein to treatment include curative, palliative and prophylactic treatment. The description which follows concerns the therapeutic applications to which the nicotinamide derivatives of formula (I) may be put.

The nicotinamide derivatives of formula (I) inhibit the PDE4 isozyme and thereby have a wide range of therapeutic applications, as described further below, because of the essential role, which the PDE4 family of isozymes plays in the physiology of all mammals. The enzymatic role performed by the PDE4 isozymes is the intracellular hydrolysis of adenosine 3',5'-monophosphate (cAMP) within pro-inflammatory leukocytes. cAMP, in turn, is responsible for mediating the effects of numerous hormones in the body, and as a consequence, PDE4 inhibition plays a significant role in a variety of physiological processes. There is extensive literature in the art describing the effects of PDE inhibitors on various inflammatory cell responses, which in addition to cAMP increase, include inhibition of superoxide production, degranulation, chemotaxis and tumor necrosis factor (TNF) release in eosinophils, neutrophils and monocytes.

Therefore, a further aspect of the present invention relates to the use of the nicotinamide derivatives of formula (I), their pharmaceutically acceptable salts and/or derived forms, in the treatment of diseases, disorders, and conditions in which the PDE4 isozymes are involved. More specifically, the present invention also concerns the use of the nicotinamide derivatives of formula (I), their pharmaceutically acceptable salts and/or derived forms, in the treatment of diseases, disorders, and conditions selected from the group consisting of:

asthma of whatever type, etiology, or pathogenesis, in particular asthma that is a member selected from the group consisting of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma and wheezy infant syndrome, chronic or acute bronchoconstriction, chronic bronchitis, small airways obstruction, and emphysema, obstructive or inflammatory airways diseases of whatever type, etiology, or pathogenesis, in particular an obstructive or inflammatory airways disease that is a member selected from the group consisting of chronic eosinophilic pneumonia, chronic obstructive pulmonary disease (COPD), COPD that includes chronic bronchitis, pulmonary emphysema or dyspnea associated therewith, COPD that is characterized by irreversible, progressive airways obstruction, adult respiratory distress syndrome (ARDS) and exacerbation of airways hyperreactivity consequent to other drug therapy pneumoconiosis of whatever type, etiology, or pathogenesis, in particular pneumoconiosis that is a member selected from the group consisting of aluminosis or bauxite workers' disease, anthracosis or miners' asthma, asbestosis or steam-fitters' asthma, chalicosis or flint disease, ptilosis caused by inhaling the dust from ostrich feathers, siderosis caused by the inhalation of iron particles, silicosis or grinders' disease, byssinosis or cotton-dust asthma and talc pneumoconiosis;

bronchitis of whatever type, etiology, or pathogenesis, in particular bronchitis that is a member selected from the group consisting of acute bronchitis, acute laryngotracheal bronchitis, arachidic bronchitis, catarrhal bronchitis, croupus bronchitis, dry bronchitis, infectious asthmatic bronchitis, productive bronchitis, staphylococcus or streptococcal bronchitis and vesicular bronchitis, bronchiectasis of whatever type, etiology, or pathogenesis, in particular bronchiectasis that is a member selected from the group consisting of cylindric bronchiectasis, sacculated bronchiectasis, fusiform bronchiectasis, capillary bronchiectasis, cystic bronchiectasis, dry bronchiectasis and follicular bronchiectasis, seasonal allergic rhinitis or perennial allergic rhinitis or sinusitis of whatever type, etiology, or pathogenesis, in particular sinusitis that is a member selected from the group consisting of purulent or nonpurulent sinusitis, acute or chronic sinusitis and ethmoid, frontal, maxillary, or sphenoid sinusitis, rheumatoid arthritis of whatever type, etiology, or pathogenesis, in particular rheumatoid arthritis that is a member selected from the group consisting of acute arthritis, acute gouty arthritis, chronic inflammatory arthritis, degenerative arthritis, infectious arthritis, Lyme arthritis, proliferative arthritis, psoriatic arthritis and vertebral arthritis, gout, and fever and pain associated with inflammation, an eosinophil-related disorder of whatever type, etiology, or pathogenesis, in particular an eosinophil-related disorder that is a member selected from the group consisting of eosinophilia, pulmonary infiltration eosinophilia, Loffler's syndrome, chronic eosinophilic pneumonia, tropical pulmonary eosinophilia, bronchopneumonic aspergillosis, aspergilloma, granulomas containing eosinophils, allergic granulomatous angiitis or Churg-Strauss syndrome, polyarteritis nodosa (PAN) and systemic necrotizing vasculitis, atopic dermatitis, allergic dermatitis, contact dermatitis, or allergic or atopic eczema, urticaria of whatever type, etiology, or pathogenesis, in particular urticaria that is a member selected from the group consisting of immune-mediated urticaria, complement-mediated urticaria, urticariogenic material-induced urticaria, physical agent-induced urticaria, stress-induced urticaria, idiopathic urticaria, acute urticaria, chronic urticaria, angioedema, cholinergic urticaria, cold urticaria in the autosomal dominant form or in the acquired form, contact urticaria, giant urticaria and papular urticaria, conjunctivitis of whatever type, etiology, or pathogenesis, in particular conjunctivitis that is a member selected from the group consisting of actinic conjunctivitis, acute catarrhal conjunctivitis, acute contagious conjunctivitis, allergic conjunctivitis, atopic conjunctivitis, chronic catarrhal conjunctivitis, purulent conjunctivitis and vernal conjunctivitis, uveitis of whatever type, etiology, or pathogenesis, in particular uveitis that is a member selected from the group consisting of inflammation of all or part of the uvea, anterior uveitis, iritis, cyclitis, iridocyclitis, granulomatous uveitis, nongranulomatous uveitis, phacoantigenic uveitis, posterior uveitis, choroiditis; and chorioretinitis, multiple sclerosis of whatever type, etiology, or pathogenesis, in particular multiple sclerosis that is a member selected from the group consisting of primary progressive multiple sclerosis and relapsing remitting multiple sclerosis, autoimmune/inflammatory diseases of whatever type, etiology, or pathogenesis, in particular an autoimmune/inflammatory disease that is a member selected from the group consisting of autoimmune hematological disorders, hemolytic anemia, aplastic anemia, pure red cell anemia, idiopathic thrombocytopenic purpura, systemic lupus erythematosus, polychondritis, scleroderma, Wegner's granulomatosis, dermatomyositis, chronic active hepatitis, myasthenia gravis, Stevens-Johnson syndrome, idiopathic sprue, autoimmune inflammatory bowel diseases, ulcerative colitis, endocrin opthamopathy, Grave's disease, sarcoidosis, alveolitis, chronic hypersensitivity pneumonitis, primary biliary cirrhosis, juvenile diabetes or diabetes mellitus type I, keratoconjunctivitis sicca, epidemic keratoconjunctivitis, diffuse interstitial pulmonary fibrosis or interstitial lung fibrosis, idiopathic pulmonary fibrosis, cystic fibrosis, glomerulonephritis with and without nephrotic syndrome, acute glomerulonephritis, idiopathic nephrotic syndrome, minimal change nephropathy, inflammatory/hyperproliferative skin diseases, benign familial pemphigus, pemphigus erythematosus, pemphigus foliaceus, and pemphigus vulgaris, prevention of allogeneic graft rejection following organ transplantation, inflammatory bowel disease (IBD) of whatever type, etiology, or pathogenesis, in particular inflammatory bowel disease that is a member selected from the group consisting of collagenous colitis, colitis polyposa, transmural colitis, ulcerative colitis and Crohn's disease (CD), septic shock of whatever type, etiology, or pathogenesis, in particular septic shock that is a member selected from the group consisting of renal failure, acute renal failure, cachexia, malarial cachexia, hypophysial cachexia, uremic cachexia, cardiac cachexia, cachexia suprarenalis or Addison's disease, cancerous cachexia and cachexia as a consequence of infection by the human immunodeficiency virus (HIV), liver injury, pulmonary hypertension of whatever type, etiology or pathogenesis including primary pulmonary hypertension/essential hypertension, pulmonary hypertension secondary to congestive heart failure, pulmonary hypertension secondary to chronic obstructive pulmonary disease, pulmonary venous hypertension, pulmonary arterial hypertension and hypoxia-induced pulmonary hypertension, bone loss diseases, primary osteoporosis and secondary osteoporosis, central nervous system disorders of whatever type, etiology, or pathogenesis, in particular a central nervous system disorder that is a member selected from the group consisting of depression, Alzheimers disease, Parkinson's disease, learning and memory impairment, tardive dyskinesia, drug dependence, arteriosclerotic dementia and dementias that accompany Huntington's chorea, Wilson's disease, paralysis agitans, and thalamic atrophies, infection, especially infection by viruses wherein such viruses increase the production of TNF-α in their host, or wherein such viruses are sensitive to upregulation of TNF-α in their host so that their replication or other vital activities are adversely impacted, including a virus which is a member selected from the group consisting of HIV-1, HIV-2, and HIV-3, cytomegalovirus (CMV), influenza, adenoviruses and Herpes viruses including Herpes Zoster and Herpes Simplex, yeast and fungus infections wherein said yeast and fungi are sensitive to upregulation by TNF-α or elicit TNF-α production in their host, e.g., fungal meningitis, particularly when administered in conjunction with other drugs of choice for the treatment of systemic yeast and fungus infections, including but are not limited to, polymixins, e.g. Polymycin B, imidazoles, e.g. clotrimazole, econazole, miconazole, and ketoconazole, triazoles, e.g. fluconazole and itranazole as well as amphotericins, e.g. Amphotericin B and liposomal Amphotericin B, ischemia-reperfusion injury, ischemic heart disease, autoimmune diabetes, retinal autoimmunity, chronic lymphocytic leukemia, HIV infections, lupus erythematosus, kidney and ureter disease, urogenital and gastrointestinal disorders and prostate diseases, scar formation in the human or animal body, such as scar formation in the healing of acute wounds, and psoriasis, other dermatological and cosmetic uses, including antiphlogistic, skin-softening, skin elasticity and moisture-increasing activities.

According to one aspect the present invention relates in particular to the treatment of a respiratory disease, such as adult respiratory distress syndrome (ARDS), bronchitis, chronic obstructive pulmonary disease (COPD), cystic fibrosis, asthma, emphysema, bronchiectasis, sinusitis and rhinitis.

According to another aspect the present invention relates in particular to the treatment of gastrointestinal (GI) disorders, in particular inflammatory bowel diseases (IBD) such as Crohn's disease, ileitis, collagenous colitis, colitis polyposa, transmural colitis and ulcerative colitis.

According to a further aspect the present invention relates also to the reduction of scars formation.

A still further aspect of the present invention also relates to the use of the nicotinamide derivatives of formula (I), their pharmaceutically acceptable salts and/or derived forms, for the manufacture of a drug having a PDE4 inhibitory activity. In particular, the present inventions concerns the use of the nicotinamide derivatives of formula (I), their pharmaceutically acceptable salts and/or derived forms, for the manufacture of a drug for the treatment of inflammatory, respiratory, allergic and scar-forming diseases, disorders, and conditions, and more precisely for the treatment of diseases, disorders, and conditions that are listed above.

As a consequence, the present invention provides a particularly interesting method of treatment of a mammal, including a human being, with a PDE4 inhibitor including treating said mammal with an effective amount of a nicotinamide derivative of formula (I), its pharmaceutically acceptable salts and/or derived forms. More precisely, the present invention provides a particularly interesting method of treatment of a mammal, including a human being, to treat an inflammatory, respiratory, allergic and scar-forming disease, disorder or condition, including treating said mammal with an effective amount of a nicotinamide derivative of formula (I), its pharmaceutically acceptable salts and/or derived forms.

The following examples illustrate the preparation of the compounds of the formula (I):

PREPARATION 1

2-Chloro-5-fluoro nicotinic acid

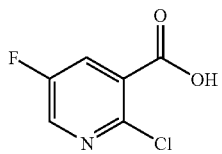

Ethyl-2-chloro-5-fluoro-nicotinoate (50.4 g, 0.247 mol) (J. Med. Chem., 1993, 36(18), 2676–88) was dissolved in tetrahydrofuran (350 mL) and a 2M aqueous solution of lithium hydroxide (247 mL, 0.495 mol) added. The reaction mixture was stirred at room temperature for 3 days. The pH of the solution was reduced to pH1 by addition of 6M hydrochloric acid and then extracted with dichloromethane (×3). The combined extracts were dried over magnesium sulphate and the solvent concentrated in vacuo to give a solid which was triturated with diethyl ether and then dried to give the title compound as a white solid, 40.56 g.

$^1$H NMR (DMSO-D$_6$, 400 MHz): δ: 8.20 (s, 1H), 8.62 (s, 1H)

MS ES+m/z 174 [MH]$^+$

PREPARATION 2

Syn-tert-Butyl4-aminocyclohexylcarbamate

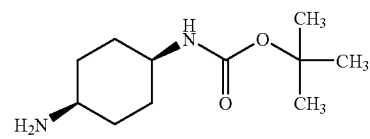

5% Palladium on charcoal (5 g) was mixed with toluene (10 mL) and was added to syn-(4-azido-cyclohexyl)-carbamic acid tert-butyl ester (170 g, 0.71 mol) (WO 99/54284, pg 80, prep 77(1)) in methanol (400 mL). The mixture was hydrogenated (80 atmospheres) at room temperature for 18 hours and then filtered. The solvent was evaporated in-vacuo and the residue was triturated with ethyl acetate (50 mL) and then with hexane (200 mL). The solid obtained was isolated by filtration, dissolved in ethyl acetate (600 mL) and filtered through Celite®. The filtrate was concentrated in-vacuo to give a slush that was diluted with hexane (300 mL). The solid obtained was isolated by filtration and was washed with ethyl acetate in hexane (20:80). The mother liquors were combined and evaporated in-vacuo, the residue was purified by chromatography on silica gel using ethyl acetate and then methanol as eluant. The material obtained was crystallised from ethyl acetate and hexane and combined with the first crop to give the title compound as a white solid, 76.0 g.

Mpt 88–90° C.

$^1$H NMR (CDCl$_3$, 400 MHz): δ: 1.41 (s, 9H), 1.52–1.77 (m, 8H), 1.82 (m, 1H), 1.97 (m, 1H), 2.61 (m, 1H), 3.62 (m, 1H), 4.59 (m, 1H),

MS ES+m/z 215 [MH]$^+$

PREPARATION 3

Methyl imidazo[1,2-a]pyridine-8-carboxylate

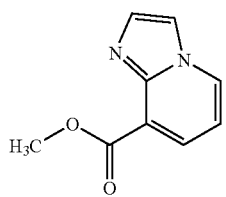

A mixture of methyl 2-aminonicotinate (WO 89/01488 pg33, prep 17) (1 g, 6.56 mmol), and chloroacetaldehyde (1.05 mL, 6.56 mmol) in ethanol (5 mL) was heated under reflux for 18 hours. The cooled mixture was diluted with water (10 mL), 0.88 ammonia (1 mL) added and the solution concentrated in vacuo. The residue was dissolved in methanol and the dark solution treated with charcoal, the mixture filtered and the filtrate concentrated in vacuo. The residue was purified by column chromatography on silica gel using dichloromethane:methanol:0.88 ammonia (97:2.5:0.5) as eluant, and the product triturated with ether, to afford the title compound, 768 mg.

$^1$H NMR (CDCl$_3$, 400MHz): δ: 4.02 (s, 3H), 6.83 (s, 1H), 7.63 (s, 1H), 7.79 (s, 1H), 8.00 (d, 1H), 8.31 (d, 1H).

MS TSP+m/z 177.2 [MH$^+$]

PREPARATION 4

Imidazo[1,2-a]pyridine-8-carboxylic acid

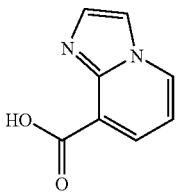

Lithium hydroxide solution (2.5 ml, 1M in water) was added to a solution of the ester from preparation 3 (400 mg, 2.27 mmol) in methanol (5 ml) and the solution stirred at room temperature for 90 minutes. The solution was concentrated in vacuo to remove the methanol, the aqueous solution acidified using 2M hydrochloric acid, and the mixture evaporated under reduced pressure to give the title compound as a yellow solid.

$^1$H NMR (DMSO-D$_6$, 400 MHz): δ: 7.60 (dd, 1H), 8.10 (s, 1H), 8.41 (d, 1H), 8.55 (s, 1H), 9.18 (d, 1H)

MS TSP+m/z 163 [MH]$^+$

PREPARATION 5

Syn-{4-[(2-chloro-5-fluoro-pyridine-3-carbonyl)-amino]-cyclohexyl}-carbamic acid tert-butyl ester

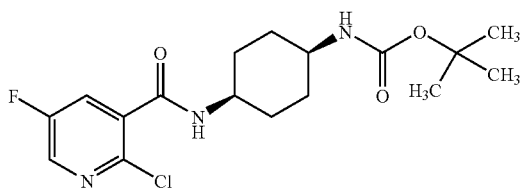

A solution of the acid of preparation 1 (8.75 g, 49 mmol) and N,N-dimethylformamide (5 drops) in dichloromethane (200 mL) was cooled to 0° C. and treated with oxalyl chloride (10.4 mL, 119 mmol) over 10 minutes. The reaction mixture was stirred at room temperature for 18 hours. The reaction mixture was concentrated in vacuo and the residue azeotroped with dichloromethane (2×). The product was taken up in dichloromethane (200 mL) and the solution treated with N-ethyldiisopropylamine (17.1 mL, 98 mmol) and the amine of preparation 2 (11.55 g, 54 mmol). The reaction mixture was stirred at room temperature for 18 hours and then washed with 10% citric acid solution (2×) and saturated sodium hydrogencarbonate solution (2×). The mixture then was dried over magnesium sulphate and concentrated in vacuo to yield the title product as a yellow solid, 18.02 g.

$^1$H NMR(DMSO-D$_6$, 400 MHz): δ: 1.21 (m, 2H), 1.32 (s, 9H), 1.51 (m, 2H), 1.73–1.88 (m, 4H), 2.63 (m, 1H), 2.83 (m, 1H), 3.60 (m, 1H), 6.63 (m, 1H), 7.86 (m, 1H), 8.44 (m, 1H)

MS ES–m/z 370 [M-H]$^-$

PREPARATION 5

Syn-(4-{[2-(2,3-dihydro-benzo[b]thiophen-6-yloxy)-5-fluoro-pyridine-3-carbonyl]-amino}-cyclohexyl)-carbamic acid tert-butyl ester

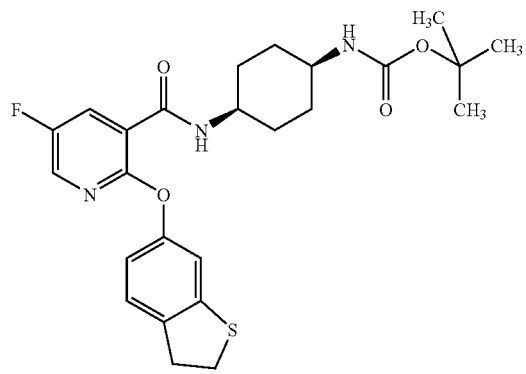

The chloro compound of preparation 5 (600 mg, 1.62 mmol), 2,3-dihydro-benzo[b]thiophen-6-ol (WO 02/18333, pg. 67, preparation 7) (245 mg, 1.62 mmol) and caesium carbonate (526 mg, 1.62 mmol) were dissolved in acetonitrile (20 mL) and the reaction mixture heated to reflux for 18 hours. The reaction mixture was concentrated in vacuo and the residue partitioned between ethyl acetate (40 mL) and water (30 mL). The organic layer was washed with brine (20 mL), dried over magnesium sulphate and concentrated in vacuo. The residue was purified by column chromatography on silica gel eluting with pentane:ethyl acetate 75:25. The crude product was triturated with ethyl acetate to yield the title product as a white solid, 589 mg.

$^1$H NMR(CDCl$_3$, 400 MHz): δ: 1.45 (m, 11H), 1.70 (m, 2H), 1.80 (m, 4H), 3.35 (t, 2H), 3.45 (t, 2H), 3.60 (m, 1H), 4.15 (m, 1H), 4.40 (m, 1H), 6.65 (m, 1H), 7.00 (s, 1H), 7.25 (d, 1H), 8.00 (m, 1H), 8.05 (d, 1H), 8.35 (m, 1H)

MS ES+m/z 510 [MNa]$^+$

PREPARATION 7

Syn-N-(4-amino-cyclohexyl)-2-(2,3-dihydro-benzo[b]thiophen-6-yloxy)-5-fluoro-nicotinamide

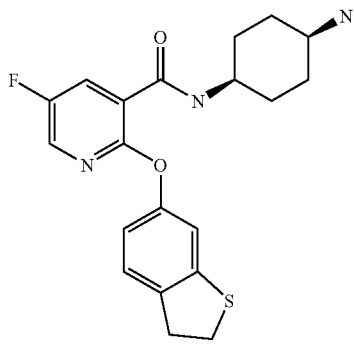

The protected product of preparation 6 (580 mg, 1.19 mmol) was dissolved in dichloromethane (4 mL) and the solution treated with trifluoroacetic acid (2 mL). The reaction mixture was then stirred at room temperature for 4 hours. The reaction mixture was diluted with toluene (5 mL) and concentrated in vacuo. The residue was partitioned between saturated sodium hydrogencarbonate solution (10 mL) and ethyl acetate (60 mL) and the organic layer washed with brine, dried over magnesium sulphate and concentrated in vacuo to yield the title product as a white solid, 500 mg.

$^1$H NMR(CDCl$_3$, 400 MHz): δ: 1.40 (m, 2H), 1.65–1.90 (m, 6H), 2.95 (m, 1H), 3.30 (t, 2H), 3.40 (t, 2H), 4.15 (m, 1H), 6.75 (m, 1H), 7.00 (s, 1H), 7.20 (d, 1H), 8.05 (m, 2H), 8.30 (m, 1H)

MS ES+m/z 388 [MH]$^+$

EXAMPLE 1

Syn-imidazo[1,2-a]pyridine-8-carboxylic acid (4-{[2-(2,3-dihydro-benzo[b]thiophen-6-yloxy)-5-fluoro-pyridine-3-carbonyl]-amino}-cyclohexyl)-amide

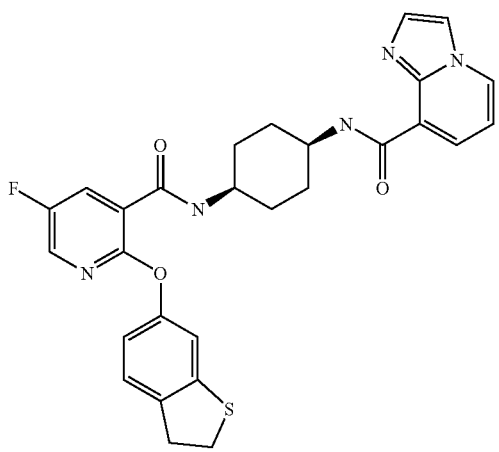

The amine of preparation 7 (150 mg, 0.39 mmol), the carboxylic acid of preparation 4 (87 mg, 0.43 mmol), 1-hydroxybenzotriazole hydrate (58 mg, 0.43 mmol), 1-(3-dimethylaminopropyl)-3-ethylcarbodiimide hydrochloride (82 mg, 0.43 mmol) and 4-methylmorpholine (47 μL, 0.43 mmol) were dissolved in dichloromethane (20 mL) and the reaction mixture stirred at room temperature for 18 hours. The reaction mixture was concentrated in vacuo and the residue dissolved in N,N-dimethylformamide (10 mL) and stirred at room temperature for 18 hours. The reaction mixture was concentrated in vacuo, the residue partitioned between ethyl acetate (50 mL) and water (30 mL) and the organic layer washed with brine, dried over magnesium sulphate and concentrated in vacuo. The residue was purified by column chromatography on silica gel eluting with pentane:ethyl acetate 85:15 to 0:100. The crude product was purified by column chromatography on silica gel again, eluting with ethyl acetate to yield the title product as a white solid, 130 mg (63%).

$^1$H NMR(CDCl$_3$, 400 MHz): δ: 1.90 (m, 8H), 3.30 (t, 2H), 3.40 (t, 2H), 4.20 (m, 1H), 4.30 (m, 1H), 6.85 (m, 1H), 7.00 (t, 1H), 7.05 (s, 1H), 7.20 (d, 1H), 7.45 (s, 1H), 7.65 (s, 1H), 8.05 (m, 2H), 8.25 (m, 2H), 8.35 (m, 1H), 10.50 (m, 1H)

MS ES+m/z 554 [MNa]$^+$

Microanalysis: Observed—C=61.99%, H=4.90%, N=12.86% C$_{28}$H$_{26}$FN$_5$O$_3$S Calculated—C=62.00%, H=5.05%, N=12.91%

EXAMPLE 2

Syn-1H-indazole-3-carboxylic acid (4-{[2-(2,3-dihydro-benzo[b]thiophen-6-yloxy)-5-fluoro-pyridine-3-carbonyl]-amino}-cyclohexyl)-amide

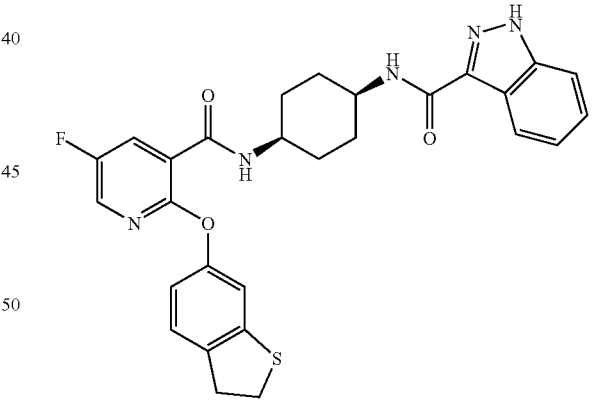

The title compound was prepared by a method similar to that described for example 1 using indazole-3-carboxylic acid in 73% yield.

$^1$H NMR(CDCl$_3$, 400 MHz): δ: 1.61–1.97(m, 10H), 2.98 (m, 2H), 3.20 (m, 1H), 3.36 (m, 1H), 6.88 (m, 1H), 6.97 (m, 1H), 7.14 (m, 2H), 7.23 (m, 1H), 7.37 (m, 1H), 7.46 (m, 1H), 8.34 (d, 2H)

MS ES+m/z 554 [MNa]$^+$

Microanalysis: Observed—C=61.27%, H=5.26%, N=13.17% C$_{28}$H$_{26}$FN$_5$O$_3$S Calculated—C=61.38%, H=4.83%, N=12.67%

EXAMPLE 3

Syn-2-(2,3-dihydro-benzo[b]thiophen-6-yloxy)-5-fluoro-N-[4-(2-hydroxy-4-methyl-benzoylamino)-cyclohexyl]-nicotinamide

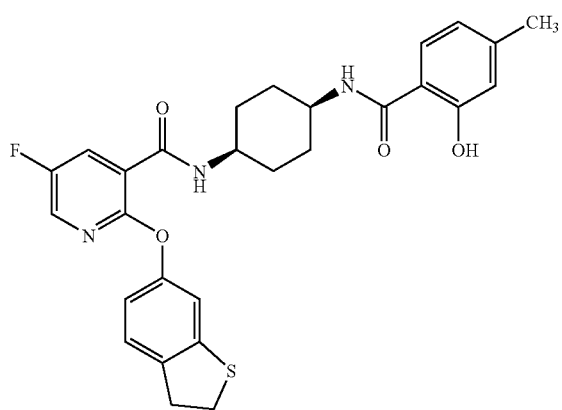

The amine of preparation 7 (150 mg, 0.39 mmol), 1-hydroxybenzotriazole hydrate (58 mg, 0.43 mmol), 1-(3-dimethylaminopropyl)-3-ethylcarbodiimide hydrochloride (82 mg, 0.43 mmol) and 4-methylmorpholine (47 μL, 0.43 mmol) were dissolved in dichloromethane (5 mL) and the solution treated with 2-hydroxy-4-methyl-benzoic acid (65 mg, 0.43 mmol). The reaction mixture was stirred at room temperature for 18 hours. The reaction mixture was partitioned between dichloromethane (40 mL) and water (20 mL) and the organic layer dried over magnesium sulphate and concentrated in vacuo. The residue was dissolved in tetrahydrofuran (5 mL), treated with 1M sodium hydroxide solution (5 mL) and stirred for 2 hours at 50° C. The reaction mixture was concentrated in vacuo and the residue taken up in ethyl acetate (50 mL) and treated with 2M hydrochloric acid (5 mL). The organic layer was washed with brine (20 mL), dried over magnesium sulphate and concentrated in vacuo. The residue was triturated with ethyl acetate to yield the title product as a white solid, 159 mg.

$^1$H NMR(CDCl$_3$, 400 MHz): δ: 1.60 (m, 2H), 1.85 (m, 4H), 1.95 (m, 2H), 2.35 (s, 3H), 3.30 (t, 2H), 3.45 (t, 2H), 4.05 (m, 1H), 4.25 (m, 1H), 5.95 (m, 1H), 6.65 (d, 1H), 6.80 (m, 2H), 7.05 (s, 1H), 7.10 (d, 1H), 7.25 (d, 1H), 8.05 (m, 2H), 8.35 (m, 1H)

MS ES+m/z 544 [MNa]$^+$

Microanalysis: Observed—C=63.75%, H=5.49%, N=7.72% C$_{28}$H$_{28}$FN$_3$O$_4$S Calculated—C=63.72%, H=5.57%, N=7.74%

In Vitro Activity of the Compounds of Formula (I)

The PDE4 inhibitory activity of the nicotinamide derivatives of the formula (I) is determined by the ability of compounds to inhibit the hydrolysis of cAMP to AMP by PDE4 (Thompson J W, Teraski W L, Epstein P M, Strada S J., "Assay of nucleotidephosphodiesterase and resolution of multiple molecular forms of the isoenzyme", *Advances in cyclic nucleotides research*, edited by Brooker G, Greengard P, Robinson G A. Raven Press, New York 1979, 10, p. 69–92). Tritium labelled cAMP is incubated with PDE4. Following incubation, the radiolabelled AMP produced is able to bind yttrium silicate SPA beads. These SPA beads subsequently produce light that can be quantified by scintillation counting. The addition of a PDE4 inhibitor prevents the formation of AMP from cAMP and counts are diminished. The IC$_{50}$ of a PDE4 inhibitor can be defined as the concentration of a compound that leads to a 50% reduction in counts compared to the PDE4 only (no inhibitor) control wells.

The anti-inflammatory properties of the nicotinamide derivatives of the formula (I) are demonstrated by their ability to inhibit TNFα release from human peripheral blood mononuclear cells (see also Yoshimura T, Kurita C, Nagao T, Usami E, Nakao T, Watanabe S, Kobayashi J, Yamazaki F, Tanaka H, Nagai H., "Effects of cAMP-phosphodiesterase isozyme inhibitor on cytokine production by lipopolysaccharide-stimulated human peripheral blood mononuclear cells", *Gen. Pharmacol.*, 1997, 29(4), p. 63). Venous blood is collected from healthy volunteers and the mononuclear cells purified by centrifugation through Histopaque (Ficoll) cushions. TNFα production from these cells is stimulated by addition of lipopolysaccharide. After 18 hours incubation in the presence of LPS, the cell supernatant is removed and the concentration of TNFα in the supernatant determined by ELISA. Addition of PDE4 inhibitors reduces the amount of TNFα produced. An IC$_{50}$ is determined which is equal to the concentration of compound that gives 50% inhibition of TNFα production as compared to the LPS stimulated control wells.

All the examples were tested in the assay described above and found to have an IC$_{50}$ (TNFα screen) of less than 300 nM. And for most of the tested compounds, they were found to have an IC$_{50}$ (TNFα screen) of even less than 100 nM.

For illustrating purpose, the following table indicates the exact IC$_{50}$ (TNFα screen) of some representative examples of the present invention:

| Example N° | IC$_{50}$ (nM) |
|---|---|
| 1 | 0.6 |
| 3 | 0.8 |

What is claimed is:
1. A compound of formula (I):

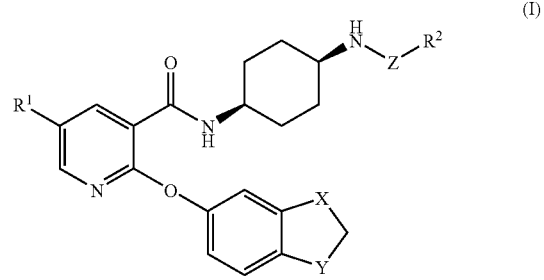

or a pharmaceutically acceptable salt thereof, wherein:
R$^1$ is H, halo or (C$_1$–C$_4$) alkyl;
X is S and Y is —CH$_2$—;
Z is CO or SO$_2$;
R$^2$ is selected from the group consisting of pyrazolyl, indazolyl, imidazolyl, and benzimidazolyl, each of which may be optionally substituted by one to three moieties independently selected from the group consisting of methyl, N(CH$_3$)SO$_2$CH$_3$, NHSO$_2$CH(CH$_3$)$_2$, hydroxyl, hydroxymothyl, chioro, fluoro, ethyl, isopropyl, methoxy, $OC_2H_4OH$, $C_2H_4OH$, $O(CH_2)_3OH$, trifluoromethyl, ethoxy, cyclopropylmethoxy and cyclopentyloxy; and $R^3$ and $R^4$ are each independently H, $(C_1-C_4)$alkyl or $SO_2(C_1-C_4\text{alkyl})$.

2. A compound of claim 1, or a pharmaceutically acceptable salt thereof, wherein $R^1$ is H, halo, $CH_3$ or $C_2H_5$.

3. A compound of claim 2, or a pharmaceutically acceptable salt thereof, wherein $R^1$ is H, F, Cl or $CH_3$.

4. A compound of claim 3, or a pharmaceutically acceptable salt thereof wherein $R^1$ is F.

5. A compound of claim 1 wherein $R^2$ is indazolyl which may be optionally substituted by one to three moieties independently selected from the group consisting of methyl, $N(CH_3)SO_2CH_3$, $NHSO_2CH(CH_3)_2$, hydroxyl, hydroxymethyl, chloro, fluoro, ethyl, isopropyl, methoxy, $OC_2H_4OH$, $C_2H_4OH$, $O(CH_2)_3OH$, trifluoromethyl, ethoxy, cyclopropylmethoxy and cyclopentyloxy.

6. A compound of claim 5, or a pharmaceutically acceptable salt thereof wherein $R^2$ is indazolyl which may be optionally substituted by one to three moieties independently selected from the group consisting of methyl and hydroxyl.

7. A compound of claim 6, or a pharmaceutically acceptable salt thereof, wherein $R^2$ is indazol-3-yl.

8. A compound of claim 1 or a pharmaceutically acceptable salt thereof, wherein Z is CO.

9. A compound of claim 1, or a pharmaceutically acceptable salt thereof, wherein:

X is S and Y is $—CH_2—$;

$R^1$ is H, halo, $CH_3$ or $C_2H_5$;

$R^2$ is selected from the group consisting of imidazolyl, indazolyl, pyrazolyl, and benzimidazolyl, each of which may be optionally substituted by one to three moieties independently selected from the group consisting of methyl, $N(CH_3)SO_2CH_3$, $NHSO_2CH(CH_3)_2$, hydroxyl, hydroxymethyl, chloro, fluoro, ethyl, isopropyl, methoxy, $OC_2H_4OH$, $C_2H_4OH$, $O(CH_2)_3OH$, trifluoromethyl, ethoxy, cyclopropylmethoxy and cyclopentyloxy; and Z is CO.

10. A compound of claim 1, or a pharmaceutically acceptable salt thereof wherein:

X is S and Y is $—CH_2—$;

$R_2$ is phenyl or indazolyl, each of which may be optionally substituted with one to three moieties independently selected from the group consisting of methyl and hydroxyl; and Z is CO.

11. A compound of claim 1, or a pharmaceutically acceptable salt thereof, wherein:

X is S and Y is $—CH_2—$;

$R^1$ is F;

$R^2$ is indazol-3-yl;

and Z is CO.

12. A compound selected from the group consisting of

Syn-1H-indazole-3-carboxylic acid (4-{[2-(2,3-dihydro-benzo[b]thiophen-6-yloxy)-5-fluoro-pyridine-3-carbonyl]amino}-cyclohexyl)-amide;

Syn-2-(2,3-Dihydro-benzo[b]thiophen-6-yloxy)-N-(4-{[5-ethyl-1-(2-hydroxy-ethyl)-1H-pyrazole-3-carbonyl]-amino}-cyclohexyl)-5-fluoro-nicotinamide;

Syn-2-(2,3-Dihydro-benzo[b]thiophen-6-yloxy)-5-fluoro-N-(4-{[1-(2-hydroxy-ethyl)-5-isopropyl-1H-pyrazole-3-carbonyl]-amino}-cyclohexyl)-nicotinamide; and Syn-1-(2-Hydroxy-ethyl)-1H-indazole-3-carboxylic acid (4-{[2-(2,3-dihydrobenzo[b]thiophen-6-yloxy)-5-fluoro-pyridine-3-carbonyl]-amino}cyclohexyl)-amide;

or a pharmaceutically acceptable salt thereof.

13. Syn-1H-indazole-3-carboxylic acid (4-{[2-(2,3-dihydro-benzo[b]thiophen-6-yloxy)-5-fluoro-pyridine-3-carbonyl]-amino}-cyclohexyl )-amide or a pharmaceutically acceptable salt thereof.

14. A pharmaceutical composition comprising a compound of claim 1 or a pharmaceutically acceptable salt thereof and a pharmaceutically acceptable excipient, diluent or carrier.

* * * * *